(12) United States Patent
Pirs et al.

(10) Patent No.: US 8,542,334 B2
(45) Date of Patent: Sep. 24, 2013

(54) VARIABLE CONTRAST, WIDE VIEWING ANGLE LCD LIGHT-SWITCHING FILTER

(75) Inventors: Janez Pirs, Ljubljana (SI); Matej Bazec, Koper (SI); Silvija Pirs, Ljubljana (SI); Bojan Marin, Ljubljana (SI); Bernarda Urankar, Dob (SI); Dusan Ponikvar, Ljubljana (SI)

(73) Assignee: Institut Jozef Stefan (SI)

( * ) Notice: Subject to any disclaimer, the term of this patent is extended or adjusted under 35 U.S.C. 154(b) by 109 days.

(21) Appl. No.: 13/208,378

(22) Filed: Aug. 12, 2011

(65) Prior Publication Data

US 2012/0002121 A1 Jan. 5, 2012

Related U.S. Application Data

(63) Continuation-in-part of application No. 11/920,323, filed as application No. PCT/EP2006/004336 on May 9, 2006, now Pat. No. 8,026,998.

(30) Foreign Application Priority Data

May 20, 2005 (SI) .................................. 200500147

(51) Int. Cl.
*G02F 1/1335* (2006.01)
(52) U.S. Cl.
USPC .......................................................... 349/96
(58) Field of Classification Search
USPC .......................................................... 349/96
See application file for complete search history.

(56) References Cited

U.S. PATENT DOCUMENTS

| | | | |
|---|---|---|---|
| 4,039,254 A | 8/1977 | Harsch | 350/160 |
| 4,696,548 A | 9/1987 | Ueno et al. | 350/338 |
| 5,249,071 A | 9/1993 | Yoshimizu et al. | 359/63 |
| 5,515,186 A | 5/1996 | Fergason et al. | 359/53 |
| 5,940,155 A | 8/1999 | Yang et al. | 349/120 |
| 2005/0142464 A1* | 6/2005 | Moriya | 430/7 |

FOREIGN PATENT DOCUMENTS

| | | |
|---|---|---|
| DE | 37 21 751 A1 | 1/1989 |
| WO | WO 95/29428 | 11/1995 |
| WO | WO 97/15254 | 5/1997 |
| WO | WO 97/15255 | 5/1997 |
| WO | WO 2004/102265 | 11/2004 |

OTHER PUBLICATIONS

International Search Report in corresponding application No. PCT/EP2006/004336 mailed Aug. 31, 2006.

(Continued)

*Primary Examiner* — Lucy Chien
(74) *Attorney, Agent, or Firm* — Renner Kenner Greive Bobak Taylor & Weber

(57) ABSTRACT

A new concept of the LCD light-switching optical filter allowing for very high, electrically controlled, continuously variable light attenuation (up to $\geq 100,000$) optimized/symmetrized for the light incidence along the normal to the LCD plane is proposed. The new LCD light-switching optical filter also exhibits very low light attenuation dependence for the oblique incidence of light within a limited cone of angles off the normal incidence direction in compliance with the international safety and quality regulation EN 379 for personal protection equipment. According to the invention the problem is solved by specific, novel modification of the general principle of highly twisted nematic LCDs, allowing for the adaptation of the light transmission/driving voltage characteristics to specific requirements of the driving electronics as well as "symmetrizing" the overall optical birefringent properties, which in turn results in a high degree of their angular compensation.

13 Claims, 6 Drawing Sheets

(56) References Cited

OTHER PUBLICATIONS

Vrecko et al: "*High Contrast Wide-Viewing Angle LCD Light Filter*" Dig. Tech. Pap. SID Int. Symp.; Digest of Technical Papers—SID International Symposium; 2005; pp. 164-167, XP002393043.

Palmer, Steven: "*Optical Angular Properties of Twisted-Nematic Liquid-Crystal Cells With Twist Angles of Less Than 90°*" Applied Optics; May 1, 1996; vol. 25, No. 13.

Office Action in corresponding U.S. Appl. No. 11/920,323 mailed Jul. 27, 2010.

Response in corresponding U.S. Appl. No. 11/920,323 as filed Sep. 27, 2010.

Office Action in corresponding U.S. Appl. No. 11/920,323 mailed Dec. 6, 2010.

Response in corresponding U.S. Appl. No. 11/920,323 as filed May 6, 2011.

Notice of Allowance in corresponding U.S. Appl. No. 11/920,323 as mailed Jun. 6, 2011.

* cited by examiner

VARIABLE CONTRAST, WIDE VIEWING ANGLE LCD LIGHT-SWITCHING FILTER

CROSS-REFERENCE TO RELATED APPLICATION

This is a Continuation-In-Part application of application Ser. No. 11/920,323 filed Nov. 13, 2007, now U.S. Pat. No. 8,026,998 which claims priority of International Application No. PCT/EP2006/004336 filed May 9, 2006, which claims the benefit of Slovenian Patent Application No. P200500147 filed May 20, 2005, all of which are incorporated herein by reference.

TECHNICAL FIELD OF THE INVENTION

The invention relates to high contrast, wide viewing angle Liquid Crystal Display (LCD) light switching filters optimized for specific requirements in particularly encountered in eye protection applications (recommendation and requirements of EN 379, . . . ) as well as to their manufacturing and operational concept.

The technical field of the present invention is the field of LCD light-switching optical filters allowing for high, electrically continuously variable light attenuation (up to ≧100,000) optimized/symmetrized for the light incidence along the normal to the LCD plane and requiring that a light blocking be effective even, when light travels through the light-switching filters within a limited cone of angles off the normal incidence direction (—see for example international safety and quality regulation EN 379 for personal protection optical devices).

Such light-switching optical filters are used in particular for applications in human eye protection (for example: welding protective filters), in stereovision and specialized optical devices. Since the LCD light filters are typically autonomous, battery powered devices, the performances such as the accuracy of the light attenuation in the optically closed (eye protective) state as well as the overall power consumption of the driving electronics strongly depend on the light transmission/voltage characteristics of the LCD light filters and its optimization is essential for achieving the state-of-the-art performances.

The above requirements are significantly different from the angular dependence issue in the technical field of LCD screens for laptop computers, monitors and TV, where rather moderate light contrasts are required and the symmetry of the light attenuation around the normal to the LCD plane is not so important (best viewing angle), while the limit of the viewing angle is typically determined as the angle of the gray scale inversion.

BACKGROUND OF THE INVENTION

The fundamentals of the above mentioned problems are well understood, because the origin of these problems is very similar to the well-known "viewing angle" problem found in Liquid Crystal Displays (LCDs) in general. Because of the very large impact of the viewing angle problem, found in liquid crystal displays (LCDs) of laptop computers and TV, worldwide interest in this problem has led to a number of solutions.

It has to be emphasized that active light filters, based on LCD light shutters are very specialized LCD products typically used for eye protection and stereovision devices. As such they are subject to noticeably different technical requirements, as found with typical LCD display applications. A point to be emphasized here is, that due to the voltage limitations, that exist for picture elements in the multiplex addressed LCD screens of lap-top computers and TV, as well as the overall user requirements for these display panels, the developed technical solutions did not lead to the desired performance and cost target for a shutter device, that has to be used for example in the personal protection devices. In the case of a shutter device for personal eye-protection applications (e.g.: welding glasses, . . . ), the drive voltage can be two to four times that of a LCD for a lap-top computer, and it is much more critical, that very high light attenuations are reached and the off-normal axis light extinction properties of the device are excellent.

The automatic LCD active light filters in their "optically closed" state (—eye protection!) usually operate in a "dark scale" regime (light attenuation>10), quite often even as two state devices in optically fully open and highly "optically closed state" (—the major issue of the presented patent application). They typically require very high light attenuation, which can be realized only with more than one (2 or even 3) LCD light shutters joint in the final protective device. Having more than one LCD light shutter in a device, significantly affects the overall problem of the angular dependence of the light attenuation as well as its symmetry around the normal to the LCD plane.

The most typical examples of stacked LCDs are found with automatic LCD light switching filters for personal protection applications in welding, where light attenuation exceeding 100,000 is required. So Harsch et al (U.S. Pat. No. 4,039,254) and Reisacher at all (DE 3721751) teach that stacking at least two standard Twist Nematic (TN) LCD (90° twist) light shutters in tandem provides the light attenuation, as required for eye protection in welding applications. None of them however discloses the advantage of the choice of the "complementary TN LCD light shutters" (complementary viewing angles), which can improve and symmetrize the overall viewing angle of the LCD welding filter.

Significantly more detailed analysis is provided in the patents of A. Hornell (WO 97/15254, WO97/15255, and WO95/29428) and in the publication by S. Palmer et al (Appl. Optics, 35, 13, (1996)). They teach that stacking two Low Twist Nematic (<90 degrees) cells (LTN LCD) provides adequate light attenuation. They further teach that the LCD cells and the adjacent crossed polarizers are mutually oriented in such a way that the polarizers are aligned exactly along the bisectrices of the LC alignment directions in both LCD cells—a solution already introduced before by Young et all (U.S. Pat. No. 5,940,155). The authors also teach that a positive-birefringent layer having its optic axis oriented in the plane of the LCD light filter is used to reduce the residual retardation of the LC cell in the optically closed state in order to reduce the driving voltage necessary for achieving high light attenuation.

The use of a different LCD technology (Pi-cell), exhibiting a significantly better angular symmetry than the above mentioned "TN and LTN solutions" is introduced for automatic LCD light filters by Fergason et al (U.S. Pat. No. 5,515,186) from OSD Envision. They teach that stacking at least two Pi-cells in a tandem provides adequate light attenuation. With the difference from the above-mentioned Hornell's patents (LTN technology) the polarizers are not aligned along the bisectrices of the LC alignment directions on the boundaries of the LCD cells. The authors also claim the use of positive-birefringent layers, having their optic axis oriented in the plane of the LCD light filter and perpendicularly to the LC-molecular alignment. Such an additional element is necessary in order to compensate for the residual birefringence of the Pi-cell in the optically closed state so that the driving voltage necessary for achieving the required high light attenuation is reduced to acceptable value. The authors also propose the specific relative orientation of the LCD cells to improve the overall angular dependence of the LCD light switching filter and even introduce the use of additional in-plane (LCD) quarter-wave plate to increase this possibility.

None of the above mentioned patents discloses the use of a negative-birefringent layer with the optic axis oriented along the normal to the LCD light filter plane (negative-birefringent c-plate) to correct for the positive birefringence of the homeotropically aligned LC molecules in the "optically closed" state of the LCD light switching filter—the major source of the annoying high angular dependence of the light attenuation of the LCD light filters. They also do not mention the use of "complementary constructed LC-cells" stacked in a tandem in order to further reduce the angular dependence of the LCD light filters. Finally none of the above mentioned technical solutions mentions nor allows a "specific optimization" (other than standard LCD panel solutions) of the LCD cell parameters (like LC-molecular orientation twist angles, relative orientation of the polarizing films with respect to the LC-molecular alignment, . . . ) to get the required value and slope of the light transmission/voltage characteristics. Since the LCD light filters are typically autonomous, battery powered devices, the performances of the driving electronics are rather limited by the possible choice of batteries. The accuracy of the adjustment of the light attenuation and especially the overall power consumption therefore strongly depend on the light transmission/voltage characteristics of the LCD light filters.

SUMMARY OF THE INVENTION

The object of the present invention is to provide a LCD light-switching optical filter allowing for very high, electrically controlled, continuously variable light attenuation (up to $\geq$100,000) optimized/symmetrized for the light incidence along the normal to the LCD plane.

High contrast and wide viewing angle in the optically closed state (eye protective state) are achieved with the LCD light switching filter according to claim 1. Advantageous embodiments of this filter are subject matter of the sub claims.

The proposed light switching filter comprises two electrically controlled optical birefringent elements—LC-cells LCD1, LCD2, two mutually crossed pairs of polarizing films (polarizer P, analyzer A) $P_1$, $A_1$ and $P_2$, $A_2$, adjacent to the light input and output sides of the said LC-cells LCD1, LCD2, as shown for example on the FIG. 8, each of the said LC-cells LCD1, LCD2 using a thin layer of liquid crystal molecules oriented in a highly twisted configuration (twist angles $\Phi$ from 120 to 240 degrees) enclosed between two boundary glass plates $1a^a$, $1a^b$, the said plates $1a^a$, $1a^b$ being on the inner side covered by transparent electrodes $1b^a$, $1b^b$ and alignment layers $1c^a$, $1c^b$, as shown for example on the FIG. 1. The whole assembly comprises also negative-birefringent compensating layers R1, R2 protective cover glass C and "photopic" filter PF reflecting harmful IR and UV light.

Key features of the proposed invention and/or its advantageous embodiments are the highly twisted Liquid Crystal (LC) molecular orientation of the LCD light shutter, its operation in the "low-slope regime LS" of the light transmission/driving voltage characteristics (FIG. 3) and the complementary dual LC-cell configuration of the LCD light switching filter (FIG. 8). The resulting overall symmetry of the proposed LCD light switching filter allows for very high, continuously electrically variable optical attenuation, as well as efficient angular compensation using just simple, low cost negative-birefringent c-plate retarders. As a result of their manufacturing process the latter exhibit also some built-in minimal positive in-plane birefringence, which is typically within 5% (<10%) of the nominal negative c-plate retardation (few ten nm). The proposed technical solutions according to the invention noticeably improve the overall optical performances of the LCD light-switching filters, which significantly exceed the highest requirements of the International Safety Standards (i.e.: EN 379, . . . ) for eye protection devices:

a. High level of light attenuation (up to $\geq$100,000) in the "optically closed" state of the filter
b. Precision continuous electrical adjustment of the light attenuation of the filter
c. Symmetrization of the light attenuation within small angles ($\leq$15°) around the normal to the LCD light filter plane,
d. Compensation for the angular dependence of light attenuation, The above features represent the most essential performance requirements for the automatic LCD light switching filters for eye protection applications. According to the invention they are very efficiently realized using LCD light shutters based on the standard STN technology optimized according to the following concept—Highly Twisted Light Shutter—HTLS:

Ad a.

Since the required high level of light attenuation can be achieved only by using two LCD light shutters in a tandem, relatively low light attenuations (45-350) are required for each of them to cover the entire protective range, as required by international standards like EN 379. So relatively low light attenuation typically achieved with STN LCDs is not a problem. Moreover, higher driving electric fields, necessary for achieving the same light attenuation as the standard TN LCD light shutters, as well as the overall HTLS operational concept, result in noticeably better homeotropic alignment of the LC molecules in the optically closed state than with the conventional TN or LTN technologies (see FIG. 7). This property can be very efficiently used to help compensating for the angular dependence of the light attenuation (see Ad d for details).

Ad b.

The most contradicting requirement seems to be the precision continuous adjustment of the light attenuation, as the light transmission/voltage characteristic of the STN LCD is generally believed to be a lot steeper than with TN or LTN technologies. However, this is true only for the relatively low light attenuation, while for the higher attenuation ($\geq$45) the slope of the light transmission/driving voltage V characteristics "levels off" (see FIG. 3) and is typically few times smaller because of the unbalanced residual retardation of the thin boundary LC molecular layers $d^a$, $d^b$, where the surface interactions compete with the driving electric field (see FIG. 1). The limiting minimum driving voltage amplitude $V_{LS}$ for the "low-slope regime" (V$\geq$$V_{LS}$; see FIG. 3) depends on the twist angle $\Phi$ and so does the overall slope of the light transmission/driving voltage characteristics (FIG. 4). This property of the STN LCDs has never been considered to be important, as the said STN LCDs were developed with only high information content LCD panels in mind, where the driving voltage V is varied in the "high-slope" regime of the light transmission/driving voltage characteristics (FIG. 3) from the switching threshold voltage $V_{th}$ to a limiting voltage $V_{LS}$ for the onset of the low-slope regime ($V_{th}$$\leq$V$\leq$$V_{LS}$). Besides the LC molecular twist angle $\Phi$ the said characteristics is also controlled by the chiral doping (see FIG. 6) of the liquid crystal ($d^a$+$d^b$+e) and/or by the relative angle $\alpha$ between the crossed polarizers and the LC-alignment (FIG. 5; see also Ad c.). The light attenuation required for the LCD light switching filters for personal protection applications (e.g. welding) is typically in the range from ~4000 to ≧100,000. With variable protective shade LCD light switching filters the light transmission in the optically closed (protective) state is therefore adjusted in the "dark scale" (higher light attenuation) rather than in the "gray scale" regime typical for the computer or TV terminals. In view of this one can optimize one, two or all three technical parameters specified above (FIGS. 4, 5 and 6) to achieve that the light transmission of the LCD light switching filter is adjustable only within the higher driving voltage, "low-slope" regime ($V \geqq V_{LS}$), as shown in the FIG. 3. Furthermore the said three technical parameters allow for adjusting the LCD light switching filter performances to optimally fit the available maximum driving voltage V span of the particular electronic driving circuitry, which is typically strongly limited by the batteries used to power the said circuitry.

Ad c.

Since the required high light attenuation can be achieved only by using a tandem of two STN LCD light shutters, the required symmetry around the normal to the filter can be further improved by using various "complementary features" of both STN LCD light shutters in the LCD light switching filter (see FIGS. 2, 8 and "Detailed description"):

1. LC Alignment Symmetry: LC alignment directions in the second STN LCD light shutter can be rotated for 90° with respect to the LC alignment in the first LCD light shutter Furthermore, the two STN LCD light shutters can be rotated for a small angle β ($\beta \leqq 15°$) with respect to each other to further reduce the asymmetry resulting from LC molecular tilt angles, . . .

2. LC Chirality Symmetry: The LC chirality in the second STN LCD cell can have an opposite sign with respect to the LC chirality in first LCD cell (e.g. first LCD cell—right handed twist, second LCD cell—left handed twist), Introducing this feature, allows further LCD light switching filter construction parameter symmetries:

Alignment Symmetry of Crossed Polarizers & LC Symmetry Axes: Relative small angle α between the LC symmetry axes and crossed polarizer axes for the first LCD light shutter can have the opposite sign as compared to the second LCD light shutter (−α)

Alignment Symmetry of the Small Intrinsic In-plane Positive Birefringence of the Compensation Films & LC Symmetry Axes: Computer modeling shows that the intrinsic in-plane positive birefringence of the negative c-plate birefringent compensation films should be aligned within a small angle γ to the normal to the residual LC in-plane positive birefringence of LC (partial compensation). Again, the said angle γ can be positive with one and negative with the second LCD light shutter.

With all other construction parameters of the proposed "tandem LCD light filter" kept identical for both LCD cells and observing the constraint that the output polarizer $A_1$ of the first LCD light shutter LCD1 is substantially parallel (within a small angle $\beta \leqq 15°$) to the input polarizer $P_2$ of the second LCD light shutter LCD2 (→full light transmission in the optically open state), the above described "symmetrization" improves the homogeneity of the light attenuation around the normal to the LCD filter plane. This feature is in particularly important for low light attenuations, where due to low driving voltages the LC molecular orientation in the central LC layer e is not homeotropic enough to be efficiently angularly compensated by the negative-birefringent c-plate compensation layer R (see FIG. 1) as described for higher light attenuations (see paragraph d below).

Ad d.

Increased homeotropic alignment of STN LCDs in the optically closed state, as compared to standard TN or LTN solutions (see FIG. 7), further simplifies the problem of angular compensation of the light attenuation allowing the use of only a simple negative-birefringent c-plate compensation layers $R_1$ respectively $R_2$ built-in between the two LC-cells LCD1 respectively LCD2 and the adjacent crossed polarizers $P_1$, $A_1$ respectively $P_2$, $A_2$. Commercially available negative-birefringent c-plate compensation layers ($R_1$, $R_2$) exhibit also some minimal built-in in-plane positive-birefringence (typically within 5% of the nominal negative c-plate retardation), which structure can be used to further improve the angular dependence of the light attenuation as well as reduce the driving voltage if properly aligned with the boundary LC layers d in the LC-cells (LCD1 and LCD2).

According to the invention the above briefly described features (a through d) that are specific for the STN LCD light shutters result in important improvement of the optical performances of the LCD light-switching filters in particularly for improving overall angular homogeneity of the light attenuation:

Computer modeling of the proposed LCD protective light filter structure, confirmed with experimental evaluation clearly shows that narrowing down the choice of the relative position of the negative-birefringent c-plate compensation layers $R_1$ and $R_2$ within the proposed LCD light filter stack (as shown in FIG. 8), not only compensates the positive birefringence of the homeotropically aligned LC molecules in the optically closed state of the LCD light-switching filter but allows also for partial compensation of the angular dependence of the crossed polarizers $P_1$, $A_1$ respectively $P_2$, $A_2$ (claims 9, 13)—see FIGS. 8, 10*a, b*.

Furthermore, commercially available negative-birefringent c-plates used for angular dependence of the light attenuation compensation typically exhibit also some (~5%) intrinsic in-plane birefringence [e.g. triacetate cellulose (TAC) lamination for polarizing films]. To avoid this typically adverse side-effect (e.g. for polarizing films), the negative-birefringent c-plates are typically laminated with the long axis of the "in-plane birefringence" parallel to the polarizing axis (→in-plane birefringence is efficiently eliminated).

According to the invention the negative-birefringent foils R1, R2 are not laminated with the long axis of their intrinsic in-plane birefringence along the polarizer axes but are laminated substantially perpendicular to the LC residual positive in-plane birefringence in the optically closed (electrically driven) state. The latter is "parallel" with the LC alignment symmetry direction ($S^1_1$ respectively $S^1_2$) of both LCD cells (LCD 1 respectively LCD2). Computer modeling further shows that such a partial compensation of the birefringent properties of the said in-plane birefringence of LCD1 respectively LCD2 and of the compensation foils R1 respectively R2 can improve the viewing angle as well as reduce the driving voltage for the LCD light switching filter (see FIG. 9).

DESCRIPTION OF DRAWINGS

This invention may be better understood and its objectives and advantages will become apparent to those skilled in the art by reference to the annexed drawings as follows.

DETAILED DESCRIPTION

Figure 1A:
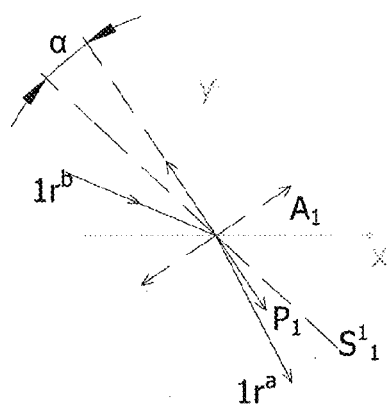
FIG. 1—Schematic presentation of the structure of HTLS optionally angularly compensated by an additional negative-birefringent layer R1, positioned accordingly to the relative orientation of the light input polarizing film and LC molecular alignment, showing in a separate picture the specific polarizing film and LC-molecular orientation in the optically closed state of the first LC-cell LCD1:
 a. Situation when the light input polarizer $P_1$ is parallel to the symmetry axis $S^1{}_1$ through the acute angle between the LC-molecular alignment directions $1r^a$, $1r^b$ of the first LC-cell LCD1
 b. Situation when the light input polarizer $P_1$ is perpendicular to the symmetry axis $S^1{}_1$ through the acute angle between the LC-molecular alignment directions $1r^a$, $1r^b$ of the first LC-cell LCD1
Figure 1A:
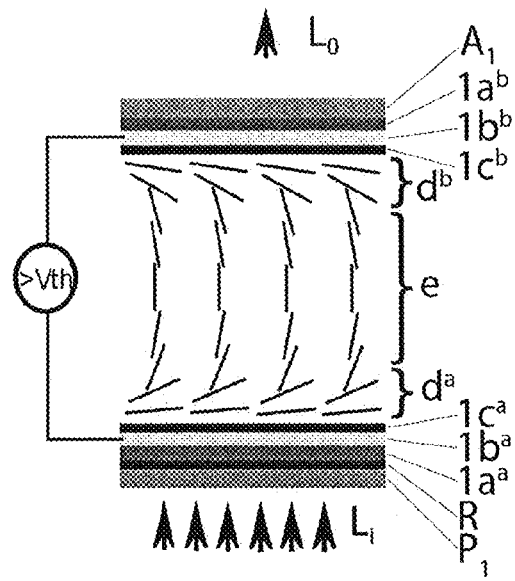
Figure 1B:
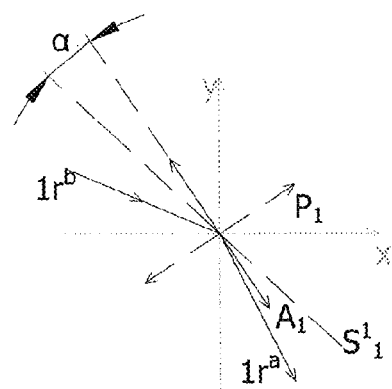
Figure 1B:
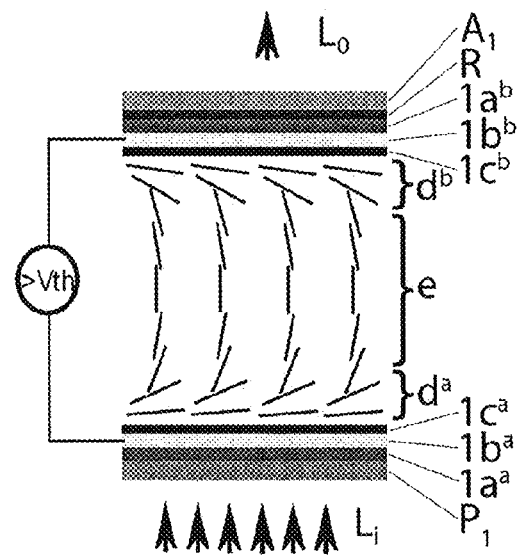

The objective of the present invention is a concept of the LCD light-switching optical filter allowing for very high, electrically controlled, continuously variable light attenuation (up to ≧100,000) optimized/symmetrized for the light incidence along the normal to the LCD plane. At the same time the new LCD light-switching optical filter has to exhibit very low light attenuation dependence for the oblique incidence of light within a limited cone of angles off the normal incidence direction (preferably ≧15°—see international safety and quality regulation EN 379 for personal protection optical devices).

According to the invention the problem is solved by specific, novel modification of the general principle of highly twisted nematic LCDs, allowing for "symmetrizing" the overall birefringent properties, which in term results in their angular compensation. In the following exemplary embodiments of the invention are described in detail using FIGS. 1-10 without limiting the scope of the claims.

High contrast and wide viewing angle in the optically closed state of the LCD light switching filters are achieved using a multilayer laminate comprising two electrically controlled optical birefringent elements—LC-cells LCD1, LCD2, two mutually crossed pairs of polarizing films $P_1$, $A_1$ and $P_2$, $A_2$, adjacent to the light input and output sides of the said LC-cells LCD1, LCD2, each of the said LC-cells LCD1, LCD2 using a thin layer of liquid crystal molecules oriented in a highly twisted configuration (twist angles Φ from 120 to 240 degrees) enclosed between two boundary glass plates $1a^a$, $1a^b$, the said plates $1a^a$, $1a^b$ being on the inner side covered by transparent electrodes $1b^a$, $1b^b$ and alignment layers $1c^a$, $1c^b$, as shown on the FIG. 1. LC-cells LCD1 respectively LCD2 have additional negative-birefringent compensating layers R1, R2 laminated between them and the adjacent polarizing films $P_1$, $A_1$ respectively $P_2$, $A_2$ in order to further improve the overall optical properties. The block diagram of such LCD light switching filter is shown in the FIG. 8.

As already pointed out before, the highly-twisted LC molecular structure has important advantages for optical light shutter applications (HTLS) as required for LCD light switching filters both from the light transmission/driving voltage characteristics (paragraph #1) as well as overall optical (paragraph #2) performances point of view:

1. A pronounced dual slope light transmission/driving voltage characteristics (FIG. 3), which is typical for highly twisted LC structures, as opposed to the standard TN LCD concept (twist angle 90 degrees), turns out to be ideal for light shutter applications. The latter typically operate as "two-state" devices in optically "fully open" and "highly closed" state. For many high performance applications (i.e. eye protection in welding, . . . ) the light attenuation in the optically closed regime however has to be more precisely adjusted to a particular application and therefore further continuous adjustment of the protective "shade" (i.e. EN 379 regulation) is necessary. The adjustments of the light attenuation are therefore done in the "dark scale" rather than in the "gray scale" regime, as found with typical display applications. The low-slope regime of operation LS (FIG. 3) of highly twisted LC structures, turns out to be ideal for continuous light attenuation control. However, the LCD light switching filter operating according to the HTLS concept has to be adapted to allow for the entire span of the required protective shades to be adjustable within the low slope regime LS. This means that the driving voltage V, applied in the optically closed state to the LC molecular layer $d^a+d^b+e$ via the transparent ITO electrodes $1b^a$ and $1b^b$ on the inner side of the light input and light output LC-cell LCD1 boundary glass plates $1a^a$, $1a^b$, is always greater than $V_{LS}$ (see FIG. 3). There are three technical parameters that can be used to optimize the light transmission vs. driving voltage characteristics of the LCD light switching filters operating according to the proposed HTLS concept:

1.1. Twist angle $\Phi$ of the LC molecular layer $d^a+d^b+e$ structure (see FIG. 4)
1.2. Relative orientation (angle $\alpha$) of the crossed polarizing films $P_1$, $A_1$ and the symmetry axes $S^1_1$, $S^2_1$ of the LC-molecular alignment surface directions $1r^a$, $1r^b$ in the LC-cell LCD! (see FIG. 5)
1.3. Chiral doping of the LC molecular layer $d^a+d^b+e$ (see FIG. 6)

In the following the above features are explained using the FIGS. 1 through 6 for one LC-cell LCD1. It is however understood that the same explanation can be used also for the second LC-cell LCD 2, which together with the LC-cell LCD1 forms the LCD light switching filter:

Ad 1.1.

Figure 4:
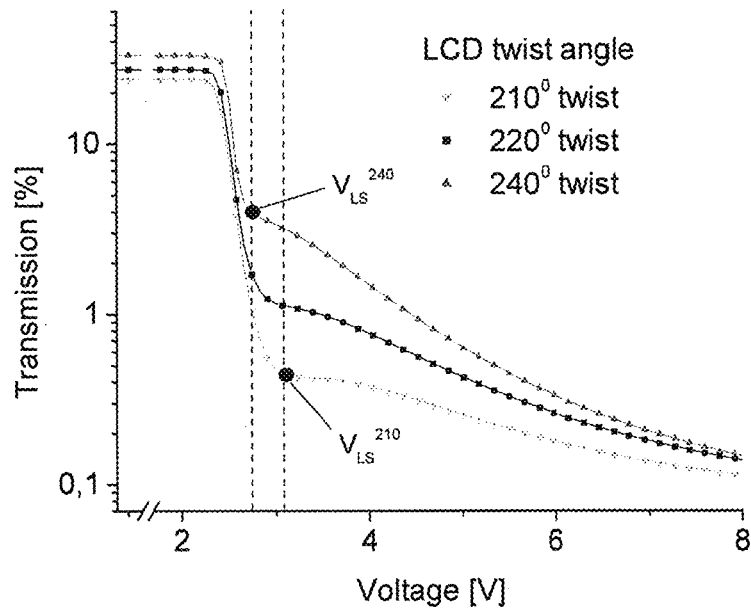

From the dependence of the light transmission/driving voltage characteristics on the molecular twist angle $\Phi$ between the molecular alignment directions $1r^a$ on the light input and $1r^b$ on the light output boundary layers $1a^a$, $1b^a$, $1c^a$ respectively $1a^b$, $1b^b$, $1c^b$ of the LC cell LCD! (see FIG. 1a) it is evident that the twist angle $\Phi$ strongly affects the slope of the said characteristics (FIG. 4). It is also shown that the limiting value $V_{LS}$ for the onset of the "low slope" regime LS (FIG. 3) varies with different values of $\Phi$ ($V_{LS}^{240}$, $V_{LS}^{210}$—FIG. 4)—the most sensitive HTLS technical parameter.

Ad 1.2.

Figure 2:
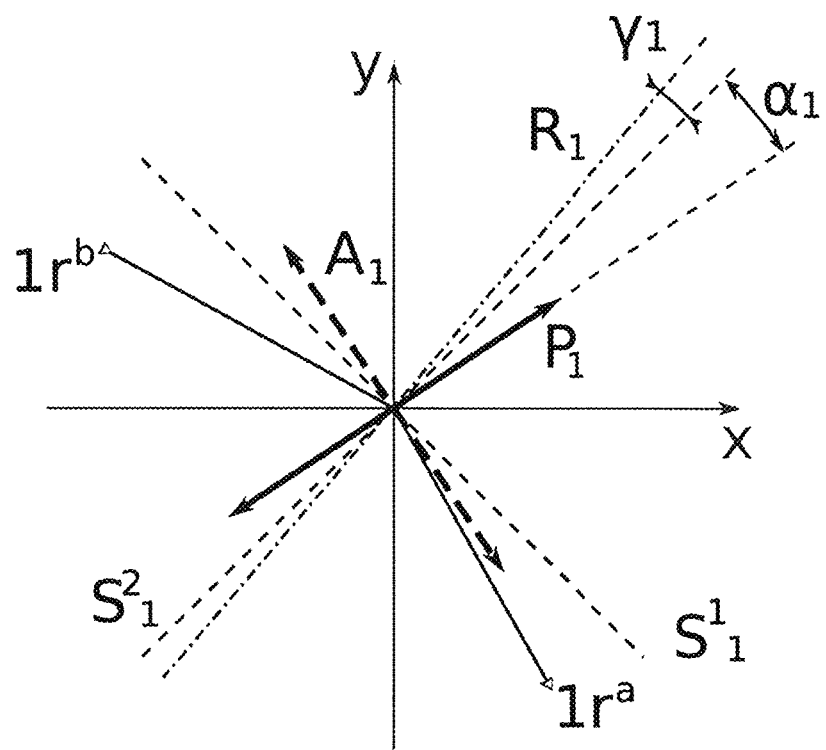
FIG. 2—Orientation of the symmetry axes ($S^1{}_1$, $S^2{}_1$) relative to the top and bottom LC cell alignment directions ($1r^a$, $1r^b$), crossed polarizers ($P_1$, $A_1$; angle α) and intrinsic positive in-plane birefringence of the negative c-plate compensation layer (angle γ)
Figure 3:
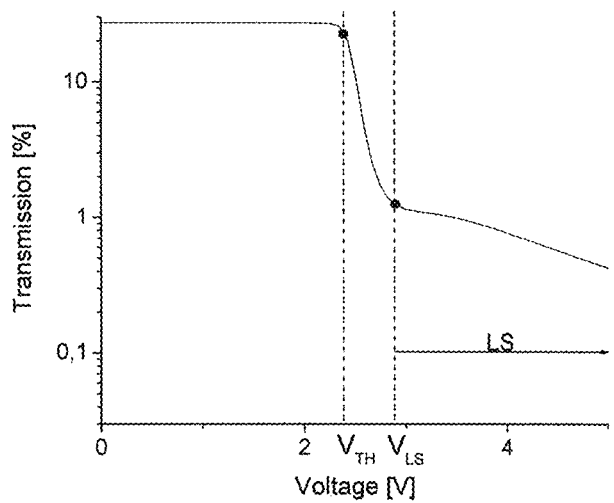
FIG. 3—Typical light transmission/driving voltage characteristics of the HTLS FIG. 4—LC twist-angle dependence of the light transmission/driving voltage characteristics FIG. 5—Effect of the relative orientation of the 220°-twisted cell and crossed polarizers on the transmission/driving voltage characteristic of the HTLS light filter FIG. 6—Effect of the chiral doping of the LC on the light transmission/driving voltage characteristic of the HTLS light filter FIG. 7—Computer modeling of the nematic LC director field at the light attenuation 320 for standard TN and 220°-twisted LCD light shutter through the LC-molecular layer FIG. 8—Block diagram of the dual complementary LC-cell protective welding light LCD filter, showing in three separate pictures adjacent to the main block diagram:
 Specific relative orientation of the crossed polarizers $P_1$, $A_1$ (angle $α_1$) and intrinsic in-plane positive birefringence of the negative c-plate compensation layer R1 (angle $γ_1$) with respect to the LC-molecular orientation symmetry axis $S^1{}_1$ through the acute angle between the LC surface orientations ($1r^a$, $1r^b$) in the optically closed state of the first LC-cell LCD1,
 Specific relative orientation of the crossed polarizers $P_2$, $A_2$ (angle $α_2$) and intrinsic in-plane positive birefringence of the negative c-plate compensation layer R2 (angle $γ_2$) with respect to the LC-molecular orientation symmetry axis $S^2{}_1$ through the acute angle between the LC surface orientations ($2r^a$, $2r^b$) in the optically closed state of the second LC-cell LCD2, as well as
 Relative orientation of the "middle" polarizers $A_1$ and $P_2$ (angle β) being parallel within a small angle $α_1$ respectively $α_2$ to the symmetry axis $S^1{}_1$ respectively $S^1{}_2$ through the acute angle between the LC-molecular alignment directions of the first LC-cell LCD1 ($1r^a$, $1r^b$) respectively the second LC-cell LCD2 ($2r^a$, $2r^b$).

The relative orientation of the crossed polarizing films $P_1$, $A_1$ and the symmetry axes $S^1_1$, $S^2_1$ of the LC-molecular alignment surface directions $1r^a$, $1r^b$ in the LC-cell LCD1, as shown on the FIGS. 1 and 2, is the next most sensitive HTLS technical parameter. The light transmission vs. driving voltage characteristics for various relative angles $\alpha$(0°, 5°, 10°) shown in the FIG. 5 demonstrates that the angle $\alpha$ between the light transmission directions of the crossed polarizing films $P_1$, $A_1$ and the symmetry axes $S^1_1$, $S^2_1$ of the LC-molecular alignment surface directions $1r^a$, $1r^b$ strongly affects the absolute value of the light attenuation.

Ad 1.3.

Figure 6:
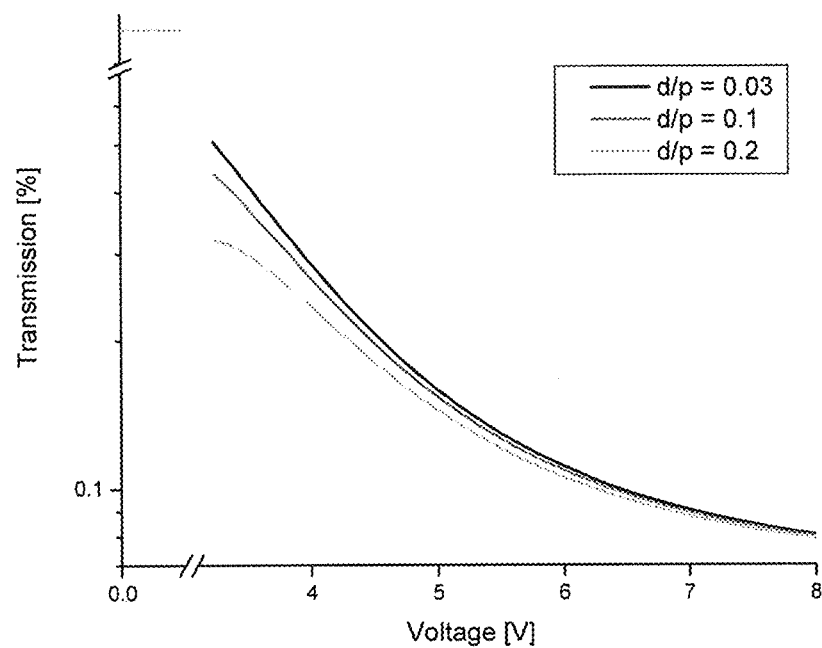

The chiral doping of the liquid crystal $d^a+d^b+e$ also affects the light transmission/driving voltage characteristics. The FIG. 6 shows the said characteristics for various values of chiral doping, where the latter is specified as the ratio d/p, where d is the thickness of the LC-cell LCD1 (typically 4-5 µm) and p is the length of the chiral pitch of the LC molecular structure induced by the chiral dopant (typically ~7 µm to 100 µm). It is obvious that the chiral doping can be also used to some extent to adapt the light transmission/driving voltage characteristics for the specific requirements of the driving electronics.

A point to be emphasized here is that the LCD light switching filters are typically autonomous, battery powered devices. Therefore the performances such as the accuracy of the light attenuation in the optically closed (eye protective) state as well as the overall power consumption of the driving electronics strongly depend on the light transmission vs. voltage characteristics of the LCD light filters. Optimization of the said characteristics is therefore essential for achieving the state-of-the-art performances. As described above, the HTLS concept provides three technical parameters ($\Phi$, $\alpha$, d/p) allowing for a precise adaptation of the light transmission vs. driving voltage characteristics—an important advantage which is not possible with standard TN or Pi-cell technologies.

2. The highly twisted LC molecular configuration in combination with the use of a dual "complementary" LC-cell filter structure (to be discussed in detail later—paragraph #3) and rotation of the crossed polarizing films away from the symmetry axes between the LC-molecular alignment directions at the LC-cell boundaries for a small angle $\alpha$, provides an additional optical symmetry essential for the low angular dependence of the light attenuation.

In the following the above features are explained using the FIGS. 1 and 2 for one LC-cell LCD1 only. It is however understood that the same explanation can be used also for the second LC-cell LCD 2, which together with the LC-cell LCD1 forms the LCD light switching filter:

The LC-cells LCD1 and LCD2 are made out of standard alkaline float glass covered with typically 40 nm thick transparent ITO electrically conductive layer widely used in the LCD industry. The LC-cells LCD1 and LCD2 are filled standard commercially available nematic liquid crystal. The highly twisted LC-molecular structure (twist angles $\Phi$ from 120 to 240 degrees) of the LC-molecular layer $d^a+d^b+e$ in the LC-cell LCD1 is obtained by doping the said nematic liquid crystal with adequate amount ($0.05 \leq d/p \leq 0.7$) of the chiral dopant. The LC-molecules in the said LC-molecular layer $d^a+d^b+e$ are further aligned by means of the polymer (typically polyimide) alignment layers $1c^a$, $1c^b$ on the conductive ITO layers $1b^a$, $1b^b$ covering the inner sides of the light input and output boundary glass plates $1a^a$ and $1a^b$ so that the alignment directions $1r^a$, $1r^b$ of the said polymer alignment layers $1c^a$, $1c^b$ make an angle $\Phi$ with respect to each other (see FIG. 1a).

The required symmetry of the light attenuation around the normal to the LC-cell LCD1 is obtained by aligning the crossed polarizing films $P_1$, $A_1$ adjacent to the outer sides of the light input and output boundary glass plates $1a^a$ and $1a^b$ of the LC-cell LCD1 along the symmetry axes $S^1_1$, $S^2_1$ of the LC-molecular alignment surface directions $1r^a$, $1r^b$ (see FIG. 2). Since the final product—LCD light switching filter employs two LC-cells LCD1 and LCD2 in order to be able to provide enough light attenuation, the crossed polarizing films $P_1$, $A_1$ can be shifted for a small angle $\alpha$ away from the said ideal orientations along the symmetry axes $S^1_1$, $S^2_1$, as the configurations of the two LC-cells LCD1 and LCD2 can be chosen such that the two LC-cells LCD1 and LCD2 compensate the optical properties of each other. Rotating the crossed polarizing films $P_1$, $A_1$ away from the ideal directions of the LC alignment symmetry axes $S^1_1$, $S^2_1$, however shifts the maximum light attenuation away from the normal to the LC-cell LCD1 plane. With a proper choice of the second LC-cell LCD2 configuration (to be described later—paragraph #3) such a shift of the angular distribution of the light attenuation results in broadening of the viewing angle of the LCD light-switching filter.

Figure 7:
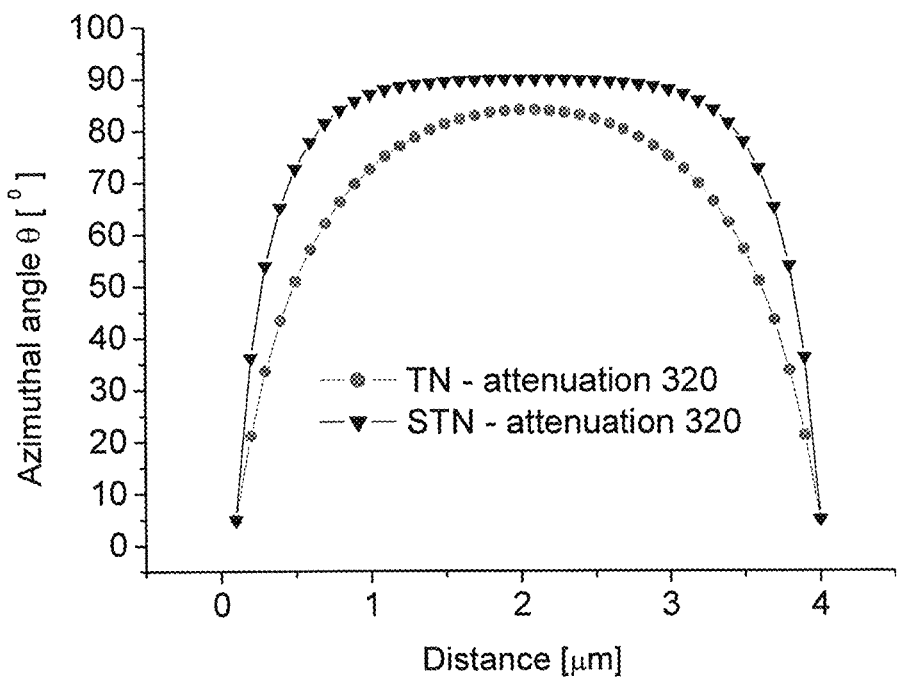

The driving voltage V necessary for achieving the specific light attenuation is typically higher with highly twisted LC structures than with standard TN LCDs. Rotation of the crossed polarizing films $P_1$, $A_1$ away from the said ideal directions of the LC alignment symmetry axes $S^1_1$, $S^2_1$ further increases the required amplitude of the driving voltage V. Therefore with the LC-cells, built according to the HTLS concept, the LC-molecular layer $d^a+d^b+e$ is subjected to noticeably higher driving voltage V, which in turn results in significantly better homeotropic alignment of the LC molecules in the optically closed state. The said advantage of the HTLS over the standard TN concept is evident from the FIG. 7 showing computer modeling of the polar angle θ(characteristic for the homeotropic orientation) of the LC director field through the LC-cell from one boundary plane to the other in the optically closed state (light attenuation 320) for the HTLS and TN LC-cell concept. As shown in the FIG. 7 the HTLS concept exhibits reasonably good homeotropic LC molecular alignment through the entire dark-scale variation, as required for adequate eye protection in the optically closed state of the LCD light switching filter (protective shades 9 through 13 according to the international EN 379 safety regulation). This feature allows for the efficient angular compensation of the LC-cell LCD1 with just a simple additional negative-birefringent layer R1, the optic axis of which is perpendicular to the LC-cell LCD1 plane. The said negative birefringent layer R1 besides being low cost, easy to manufacture and easy to be tuned to the specific LC-cell, also allows for some superior optical properties (lower light scattering, higher light attenuation, . . . ) compared to the more sophisticated retardation films widely used in the computer and TV industry.

In order to compensate for the angular dependence of the optically birefringent layers (LC-molecular layer, polarizing films, compensating negative-birefringent layer) forming the LCD light switching filter one has to "match" the positive-birefringent properties of the homeotropically aligned central layer of liquid crystal e (see FIG. 1a and FIG. 7) and the inherently negatively-birefringent polarizing films $P_1$, $A_1$ with the compensating negative-birefringent layer R1. The said layer 121 must have the optic axis perpendicular to the LC-cell LCD1 plane and has to be incorporated between the boundary glass plates $1a^a$, $1a^b$ of the LC-cell LCD1 and the adjacent polarizing film $P_1$ or $A_1$. The birefringent optical properties of the said birefringent layers depend on the difference Δn between the refractive indices of the ordinary and extraordinary light ray in the said birefringent layers and their thickness d. In the explanation the following notations will be used: $\Delta n_e^+$ and $d_e^+ \rightarrow$ difference of the refractive indexes and layer thickness of the homeotropically aligned part of the LC-molecular layer e, $\Delta n_p^-$ and $d_p^- \rightarrow$ difference of the refractive indexes and layer thickness of the polarizing films $P_1$, $A_1$, $\Delta n_R^-$ and $d_R^- \rightarrow$ difference of the refractive indexes and the layer thickness of the negative-birefringent layer R1:

2.1. In the first approximation the absolute value of the negative optical retardation ($\Delta n_R^- \times d_R^-$) of the said negative birefringent layer R1 is chosen to be equal to the difference between the absolute value of the positive optical retardation ($\Delta n_e^+ \times d_e^+$) of the homeotropically aligned part of the liquid crystal molecular layer e and the absolute value of the negative optical retardation ($\Delta n_p^- \times d_p^-$) of the polarizing films $P_1$, $A_1$. In this case only the major contribution to the angular dependence originating from the ~homeotropically aligned central part of the LC-molecular layer e is compensated, while the angular dependence of the crossed polarizing films and the thin LC-molecular layers $d^a+d^b$ at both boundary surfaces $1c^a$, $1c^b$ remain uncompensated.

2.2. The HTLS structure in the optically closed state exhibits rather high effective residual positive-birefringence in the plane of the LC-cell LCD1, as opposed to the standard TN LCD, where the said effective residual positive birefringence cancels out in the first approximation. The existence of the said residual positive-birefringence in the plane of the LC-cell LCD1 allows also for a higher order of angular compensation using tunable negative-birefringent layer The relative positioning of the negative-birefringent layer R1 between the LC-cell LCD1 and the adjacent polarizing films $P_1$, $A_1$ is in principle not arbitrary. A simple qualitative evaluation of the optics of such LCD light switching filter using "Pointcare sphere" concept shows that one can make advantage of the rather high effective residual positive-birefringence of the thin boundary LC layers $d^a+d^b$ to compensate for the angular dependence of the crossed polarizing films. In combination with a positive-birefringent layer having its optic axis perpendicular to the LC-cell plane the said residual birefringence can help reducing the angular dependence of the light attenuation of the crossed polarizing films $P_1$ and $A_1$. The computer modeling of the HTLS LC-cell as described above using GNU LCM-2 modeling software, shows that the value of the effective residual positive-birefringence of the thin boundary LC layers $d^a+d^b$ (≈80 nm of effective optical retardation) is not sufficient (about 40% too small) for the complete compensation. However even as it is, it can still strongly improve the said angular dependence of the light attenuation of the crossed polarizing films $P_1$ and $A_1$. Instead of adding the above mentioned additional positive-birefringent layer, one can simply "under-compensate" the positive birefringence of the central homeotropically aligned LC layer e, as compared to the condition specified in the preceding paragraph (2.1.) and the resulting overall positive-birefringence can do the job. The whole situation on this level of approximation is rather complex and only the computer modeling can provide a reliable estimate. It shows that any value of "under-compensation" from 100 to 300 nm will significantly improve the overall angular dependence of the LCD light switching filter.

3. All the above discussed principles of angular compensation of the optical performances are based on the fact that high light attenuation requirements, require the use of two LC-cells in the LCD light-switching filter design. Since these two LC-cells can be constructed such that their optical properties compensate each other to a great deal, just a reasonable improvement of the optical properties of each one of them can result in exceptional performances for the very specific "niche" application. All the above discussed principles of angular compensation of the optical performances can be further upgraded by the fact that the need for extremely high light attenuation (~4000 to ≧100,000 times), requires the use of the tandem of two LC-cells in the LCD light-switching filter design. Since these two LC-cells can be constructed such that their optical properties compensate each other to a great deal, just a reasonable improvement of the optical properties of each one of them can result in exceptional performances for the very specific "niche" application. In the case of the LCD light switching filters for eye protection applications the concept of the construction of the "complementary" HTLS LC-cells can get rather complex as the STN LCD technology allows not only for the adjustments of the light transmission vs. driving voltage characteristic but also provides reasonable freedom in modifying the LC molecular alignment (arbitrary direction of the viewing angle, surface pretilt, ... ) as well as LC structure itself (chirality, elastic constants, ... ):

3.1. LC Alignment Symmetry: LC alignment directions in the second STN LCD light shutter (e.g. $2r^a$, $2r^b$) are rotated for 90° with respect to the LC alignment in the first LCD light shutter (e.g. $1r^a$, $1r^b$)—see FIGS. 1, 2.

Figure 8:
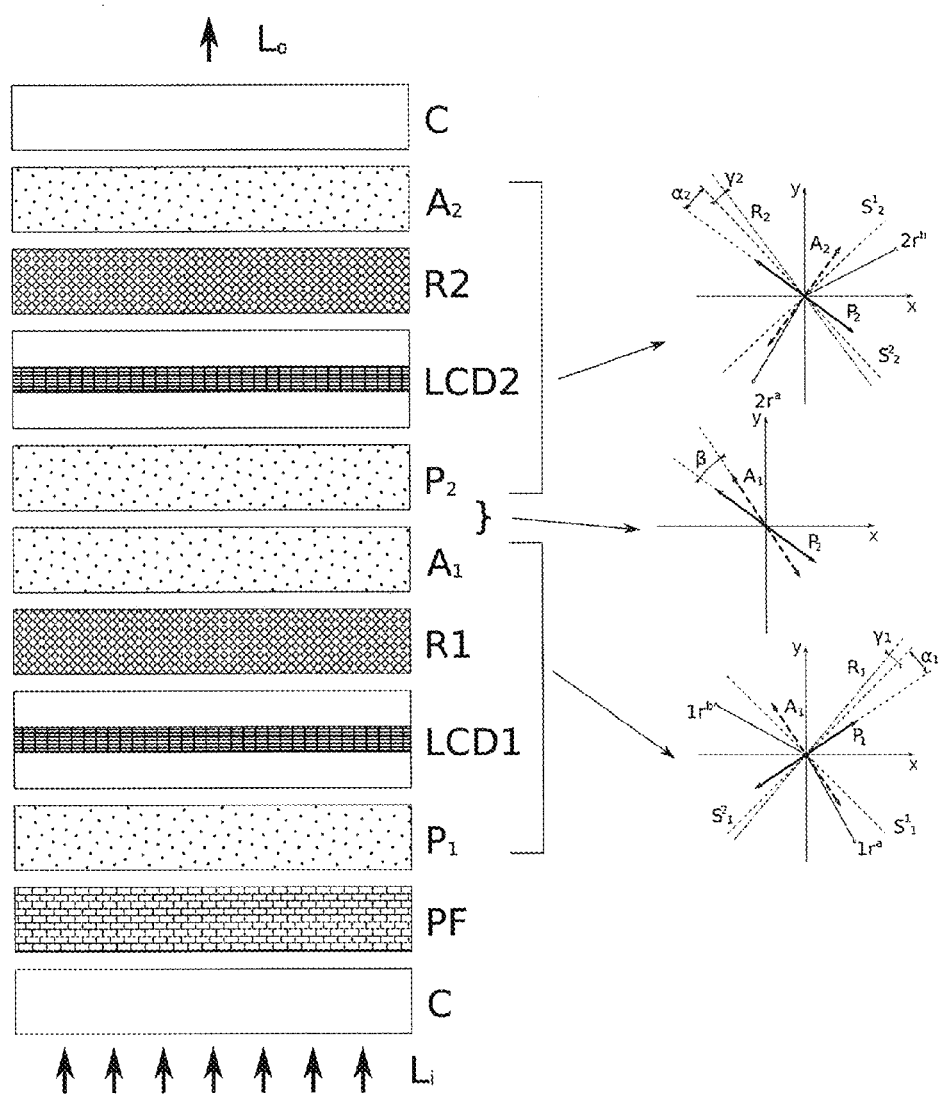

Furthermore, the two STN LCD light shutters can be rotated for a small angle β (β≦15°) with respect to each other (see FIG. 8). This small "misalignment" angle β between the LC-alignment directions $1r^a$, $1r^b$ as well as the polarizing films $P_1$, $A_1$ of the first LC-cell LCD1 and the LC-alignment directions $2r^a$, $2r^b$ as well as the polarizing films $P_2$, $A_2$ of the second LC-cell LCD2 needs a further comment. The fact is that it may turn out that the symmetry of the viewing angle would not coincide with the geometry of the LCD light filter. In order to correct for this, the crossed polarizing films $P_1$, $A_1$ and $P_2$, $A_2$, adjacent to the light input and output sides of the said LC-cells LCD1, LCD2 can be laminated to the two LC-cells so that the light output $L_0$ polarizing film $A_1$ laminated on the first LC-cell LCD1 is not perfectly aligned with the light input $L_1$ polarizing film $P_2$ on the second LC-cell LCD2. As long as the said misalignment angle β is reasonably small (≦15°) the light loss due to such a misalignment is negligible, however some additional symmetry of the light attenuation correlated with the overall geometry of the LCD light switching filter can be gained.

Figure 5:
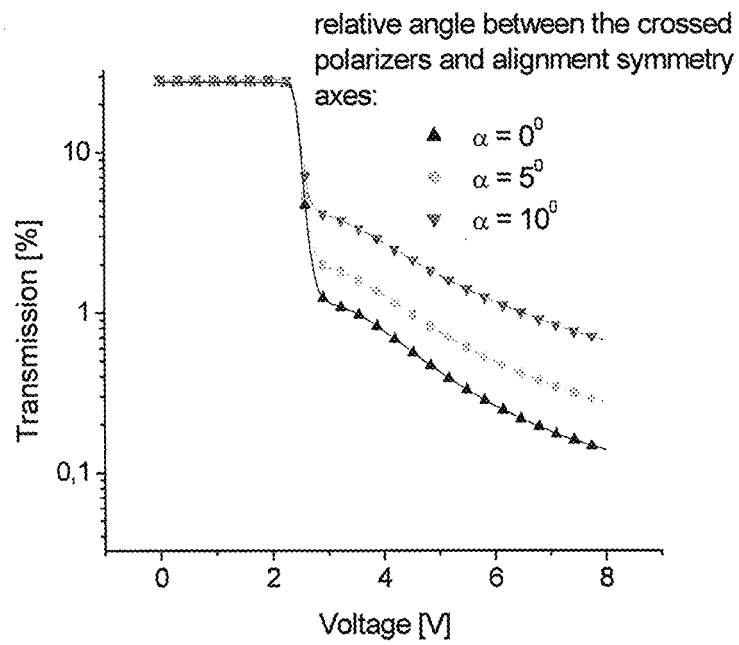

3.2. LC Chirality Symmetry: The LC chirality in the second STN LCD cell can have an opposite sign with respect to the LC chirality in first LCD cell (e.g. first LCD cell—right handed twist, second LCD cell—left handed twist), Introducing this feature, allows further LCD light switching filter construction parameter symmetries:

3.2.1. Alignment Symmetry of Crossed Polarizers & LC Symmetry Axes: Relative small angle α between the LC symmetry axes and crossed polarizer axes is introduced for adjustments of the light transmission vs. driving voltage characteristics (FIG. 5). In the case of LCD light shutters with reversed chirality the first LCD light shutter can have the opposite sign (+α) as compared to the second LCD light shutter (−α).

3.2.2. Alignment Symmetry of the Small Intrinsic In-plane Positive Birefringence of the Compensation Films & LC Symmetry Axes: Computer modeling shows that the intrinsic in-plane positive birefringence of the negative c-plate birefringent compensation films, if aligned within a small angle γ to the normal to the residual LC in-plane positive birefringence of LC, can be used to partially compensate the residual in-plane LC birefringence in the optically closed state of the LC-cells (-increased viewing angle as well as reduced the driving voltage—see example 2 and FIG. 9). In the case LCD light shutters with reversed chirality the first LCD light shutter can have the opposite sign (+γ) as compared to the second LCD light shutter (−γ).

The use of the proposed HTLS technical solution can be best demonstrated by its application in the automatic LCD light switching filter for eye protection in various welding and plasma cutting applications. Typical working embodiments are described in the Examples 1-3 and illustrated in the FIG. 8 as follows:

Example 1

The above described HTLS concept for automatic LCD light filters is in particularly ideal for eye protection in welding applications. Personal protective devices like this have to comply with the international safety regulations like EN 379, ICNIRP "Guidelines on limits of exposure to broadband incoherent optical radiations", . . . Therefore they have to allow for the adjustment of the protective "shade" in the optically closed (protective) state in a rather broad range from ~4000 up to ≧100,000 times. Furthermore they also have to protect the user not only against strong visible light flashes but also against excessive incoherent light in the invisible but harmful UV and IR light spectrum causing permanent damage to the human eye. The electro-optically active LCD light shutters cannot fulfill the above requirements only by themselves, as they are based on the use of polarizing films, which are developed to be efficient more or less only in the visible light spectrum—an additional protection against invisible UV and IR light is necessary. Since one is dealing with relatively high intensity light sources, this additional protection is preferably achieved by a filter, exhibiting selective reflection rather than absorption in the IR and UV spectral range, while being transparent in the visible spectral range, simulating more or less the eye sensitivity curve—"~photopic filter". Such an additional passive selective "mirror" furthermore guarantees permanent eye protection irrespective of the potential malfunctioning of the active LCD light filtering in the visible spectrum.

In view of this the present state-of-the-art LCD light-switching filters allowing for variable protective shade are typically made as multilayer laminates of at least two electrically controlled optical birefringent elements—LC-cells, adequate number of mutually crossed pairs of polarizing films, adjacent to the light input and output sides of the said LC-cells and on the outer sides having protective cover glass plates, one of which having on its inner side a thin film "photopic" filter layer reflecting harmful IR an UV light (see the block diagram on the FIG. 8).

The electrically controlled optical birefringent elements—LC-cells (FIG. 1), which represent the key subcomponets of the LCD light switching filter, are made according to the standard STN LCD production process, using soda-lime glass as the LC-cell boundary plates $1a^a$, $1a^b$. In order to generate the driving electric field across the LC layer $d^a+d^b+e$, the boundary glass plates $1a^a$, $1a^b$ are covered with the transparent ITO electrodes $1b^a$, $1b^b$, preferably exhibiting a surface resistivity typically 50 Ohm/square. The said electrodes are further covered with typically 50 nm thick, low residual DC voltage (RDC) polyimide like SE 4792 (Nissan). The top and the bottom polyimide alignment layers $1c^a$, $1c^b$ are then rubbed in a standard way to induce the required LC-alignment directions $1r^a$, $1r^b$ making a twist angle Φ=225° and sealed together with a perimeter seal using 4-5 μm spacers to form a LC-cell. The latter is further filled in vacuum with liquid crystal, preferably a specialized STN mixture like MLC-14000-100 (Merck). In order to stabilize the highly twisted LC-molecular orientation the said liquid crystal is doped with 0.95% of the chiral dopant like S811. The fill hole is further sealed with UV curable sealant like NOA 61(Norland). Both LC-cells LCD1 and LCD2 are manufactured in the same way except that LC-alignment directions $2r^a$, $2r^b$ in the second LC-cell LCD2 are swapped for 90 degrees with respect to the alignment directions $1r^a$, $1r^b$ of the first LC-cell LCD1 (-complementary structure). A high contrast polarizing film $P_1$ like LLC2-5618 (Sanritz) is laminated on the light input boundary glass $1a^a$ of the LC-cell LCD1 so that its light-transmitting axis is aligned to be 6 degrees away from perpendicular direction to the symmetry axis $S^1_1$ of the LC-alignment directions of the said LC-cell LCD1. The same procedure is repeated for the polarizing film P$_2$ on the light input side of the second LC-cell LCD2 its light-transmitting axis being again aligned to be 6 degrees away from perpendicular direction to the symmetry axis S$^1_2$ of the LC-alignment directions of the said second LC-cell LCD2 (see FIG. 8). The negative-birefringent layer R1, having its optic axis perpendicular to the LC-cell LCD1 plane, is subsequently laminated on the light output side of the boundary glass plate 1$a^b$ of the LC-cell LCD1. The same process is repeated for the negative-birefringent layer R2 laminated on the second LC-cell LCD2. The same kind of polarizing films (LLC2-5618) are further laminated as the light output polarizing films A1 and A2 on the light output sides of the negative-birefringent layers R1 respectively R2. The two assemblies of LC-cells comprising LC-cells LCD1 and LCD2 with the corresponding polarizing films P$_1$, A$_1$ respectively P$_2$, A$_2$ and negative birefringent c-plate layers R1 respectively R2 are subsequently laminated together so that the light output polarizing film A$_1$ of the first assembly and the light input polarizing film P$_2$ of the second assembly are aligned parallel to each other. Since, due to the specific manufacturing process the negative birefringent c-plate compensation layers exhibit also some intrinsic minimal positive in-plane birefringence, the latter was aligned with the crossed polarizers (effect—minimized). Finally the whole laminate is covered with the protective glass plates C, the protective glass plate on the light input side being on the side facing the polarizing film P$_1$ covered with a multilayer photopic filter PF selectively reflecting the light in the IR and UV spectrum while transmitting the visible light.

In order to allow for optimal angular compensation of the light attenuation in the optically closed state of the above described LCD-light switching filter for personal protection in welding applications, the values of the compensating negative-birefringent layers R1 and R2 have the same optical retardation, which is matched with the positive-birefringent retardation ($\Delta n_e^+ \times d_e^+$) of the homeotropically aligned central layer e of the liquid crystal and the inherent negative-birefringent retardation ($\Delta n_p^- \times d_p^-$) of the polarizing films P$_1$, A$_1$ and P$_2$, A$_2$ in such a way that the absolute value of the optical retardation ($\Delta n_R^- \times d_R^-$) of the optical compensating layers R1 (=R2) is 200 nm smaller than the difference of the absolute values of the retardation of the homeotropically aligned central layer e of the liquid crystal ($\Delta n_e^+ \times d_e^+$) and the inherent retardation ($\Delta n_p^- \times d_p^-$) of the polarizing films P$_1$, A$_1$ and P$_2$, A$_2$ (for detailed definitions and notations see paragraph #2, in particularly 2.2 and 2.3 of the Detailed description):

$$|(\Delta n_e^+ \times d_e^+) - (\Delta n_p^- \times d_p^-)| = |(\Delta n_R^- \times d_R^-)| + 200\ nm.$$

As described in detail in the paragraph #2, the resulting effective positive birefringence (200 nm) with the optic axis perpendicular to the LCD light switching filter plane together with the in-plane effective residual retardation of the boundary layers d$^a$, d$^b$ of the LC-molecular layer allow for very efficient overall angular compensation of the light attenuation of the LCD light switching filter in the optically closed state.

Example 2

Figure 9:
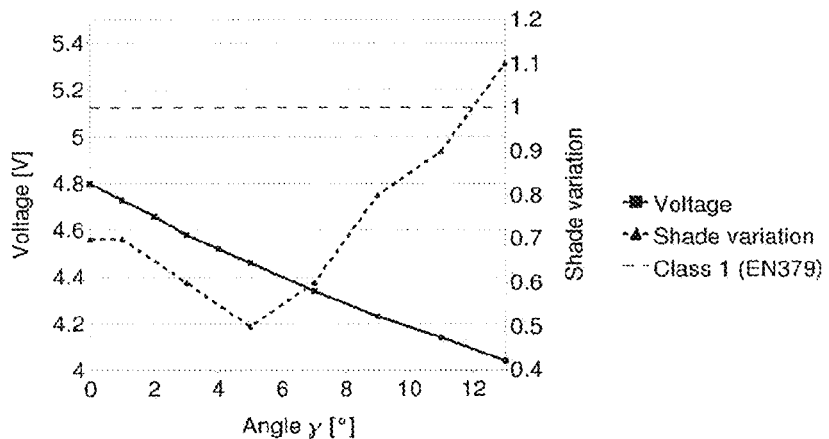
FIG. 9—Dependence of the amplitude of the electric driving voltage and protective shade homogeneity (variation) of the LCD filter on the relative orientation (angle γ) of the intrinsic in-plane positive birefringence of the negative c-plate compensation layer R.
Figure 10:
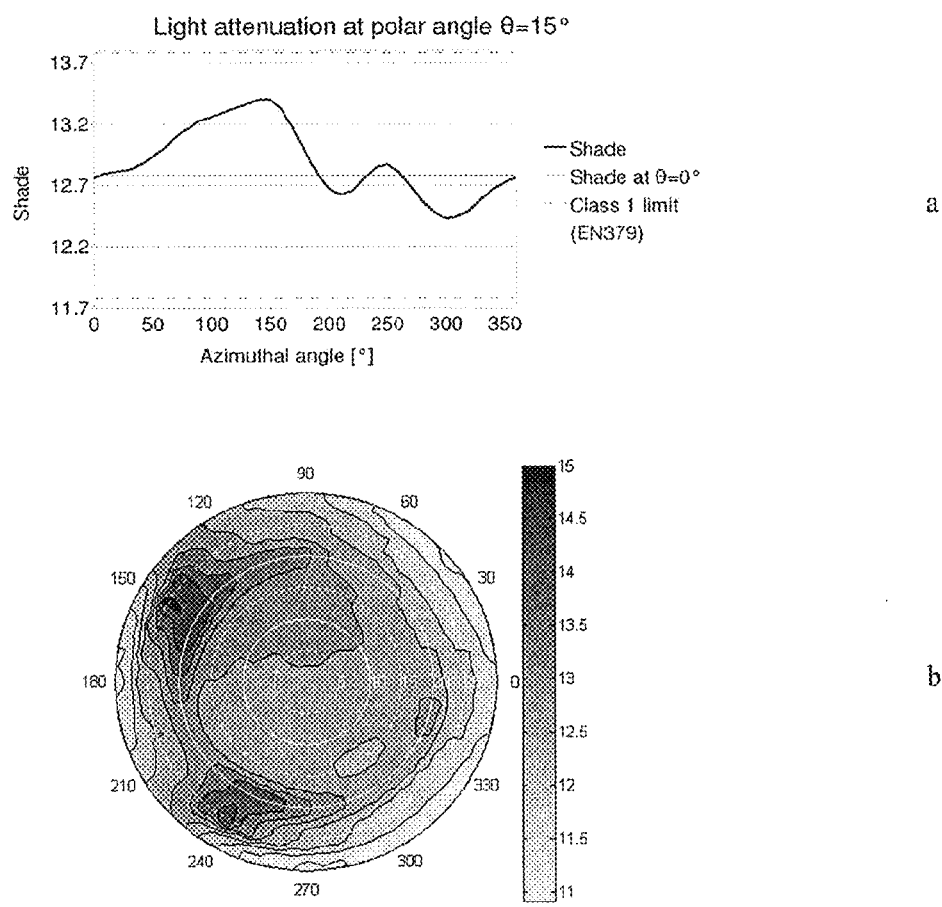
FIG. 10—Measurement of the protective shade homogeneity for the slant angle light incidence according to the EN 378 standard:
 a. Azimuth (Φ) angular dependence of the light attenuation 120,000 (Shade 13 according to EN 379) for a limiting slant angle light incidence (Θ=15° according to EN 379)
 b. Angular dependence of the light attenuation in polar angle Θ and azimuth angle Φ presentation; light attenuation at normal light incidence (Θ=0) is 120,000 (Shade 13 according to EN 379)

The same explanation and description applies as with the example 1. The difference is in the orientation of the negative c-plate retarder (R$_1$, R$_2$):

As has been already pointed out, negative c-plate birefringent compensation films (R$_1$, R$_2$) used to enhance the viewing angle typically exhibit also intrinsic, built-in "minimal" in-plane birefringence (~5% of the nominal negative c-plate retardation—few ten nm; typically 20-30 nm). It is the essence of the present continuation-in-part patent application to make advantage of the above mentioned feature (summary: p1, 1. 25-33). Instead of aligning the intrinsic positive in-plane birefringence of the negative c-plate birefringent compensation films (R$_1$, R$_2$) with the crossed polarizers in order to minimize its impact, the latter is rather aligned to be substantially perpendicular within a small angle γ ($\leq 12°$) to the positive residual in-plane birefringence of the LC. Since the absolute value of the intrinsic positive in-plane birefringence of the compensation films (R$_1$, R$_2$) turns out to be of the same order of magnitude as the positive residual birefringence of the boundary LC layers d$^a$, d$^b$ within LCD-cells LCD1 respectively LCD2 (see FIG. 1), such a relative alignment of LC and negative retarder (R$_1$ respectively R$_2$) helps "compensating" the residual birefringence of the boundary layers of the LC within LCD-cells LCD1 respectively LCD2, in the optically closed state of the LCD light-switching filter. This feature in turn helps reducing the driving voltage by $\geq 10\%$ and further improving the angular homogeneity of the light attenuation (see FIG. 9 and FIG. 10$a$, $b$), as can be explained by the computer modeling of the angular dependence of the light attenuation in the case of a slant angle light incidence. The modeling results presented in FIG. 9 clearly show that there is some optimum in such a partial compensation of the birefringent properties of the said residual in-plane birefringence of the LC-cells LCD1 or LCD2 and of the compensation foils R1 or R2:

On one side the modeling shows a tendency of decreasing the driving voltage V by rotating the optic axis of the intrinsic positive in-plane birefringence of the compensation films (R$_1$, respectively R$_2$) away from the LC symmetry axes (S$^1_1$ respectively S$^1_2$) for a small angle γ (γ$_1$ respectively γ$_2$) in the same sense as the twist angle Φ of LC molecular orientation (see FIG. 1, 2). This feature can be also confirmed by computer modeling showing that with left-handed LC-cells the angle γ is preferably positive and with the right handed LC-cells the angle γ is preferably negative.

on the other side the angular variation of light attenuation tends to be degraded with the increase of the angle γ. FIG. 9 shows the results of computer modeling of the "Shade 13 variation" as a function of the said angle γ. The "Shade 13 variation" is calculated for the case of light incidence along 15° cone around the normal to the LC-cells' plane (—limiting light incidence angle according to EN 379 regulation). The variation is defined as [(Shade$^{15°}_{min}$ − Shade$^{0°}$)/Shade$^{0°}$], where Shade$^{15°}_{min}$ represents the minimum shade value on the 15° cone of light incidence and Shade$^{0°}$ stands for the Shade for the light coming along the normal to LC-cells' plane. The "Shade variation" first tends to decrease and for γ $\geq 5°$ again tends to increase. At angle γ~12° the variation of light attenuation reaches the value 1 that represents the limit for the "first class performance" according to EN 379 regulation.

The final conclusion of this evaluation is that the optimum relative angle γ between the optic axes of the residual in-plane positive birefringence of the LC-cells LCD1 or LCD2 and the intrinsic in-plane positive birefringence of the compensation foils R1 or R2 is ≈5° and that it has to be smaller than ≈12°.

The measurements of the driving voltage for the automatic LCD light-switching filter necessary to achieve the protective shade 13 (120,000 times) according to the international regulation EN 379 clearly show that the above described orientation of intrinsic positive in-plane birefringence of the negative retarder R (within small angle γ$_1$, γ$_2$~5°) along the normal to the LC symmetry axes ($S^1_1$, respectively $S^1_2$,) reduces the driving voltage for ~0.7V (from 5.9 V to 5.2 V).

Since the LCD protective filters for eye protective applications (e.g. welding, . . . ) are typical portable, battery driven devices, the above reduction of the driving voltage is exceptionally important! The state-of-the-art batteries (e.g. Li-batteries) can provide 3V per cell and a 6V driving represents ~a limit for practical technical solutions. In order to overcome some unavoidable voltage drop in the driving electronics and still make full use of the battery life time, the driving voltage below 5.5 V is almost a must!!

The proposed solution according to the invention clearly solves the technical problem of supporting battery life time as well as allows for manufacturing LCD light-switching filters for personal protection applications that comply with the highest optical quality requirements related to the angular homogeneity of the protective shade according to International standard EN 379 and a like.

Example 3

The same explanation and description applies as with the example 1. The difference is in the orientation of the negative c-plate retarder ($R_1$, $R_2$) and with the difference from Example 2 also in introduction of additional possible symmetries of LCD light shutters and higher symmetry of their structure as a result of the symmetry in LC (±chirality) that can further increase the optical performance of the LCD light-switching filters for personal protection applications.

The complementary properties of both LCDs being first introduced by relative rotation of the LC alignment for 90° in claims 6-10) as well as in the "Summary" of this patent application can be further upgraded by introduction of the complementary rotation of the LC alignment (chirality symmetry: first LCD cell—left handed twist; second LCD cell—right handed twist—claims 11-14). Such an expanded symmetrization of the LCD light protective filter structure in turn allows further symmetrization of other structural parameters:

Relative rotation of the crossed polarizers ($P_1$, $P_2$, . . . ) for the small angle α with respect to the LCD cells' ($LCD_1$ and $LCD_2$) symmetry axes ($S^1_1$, $S^2_1$ respectively $S^1_2$, $S^2_2$)→$S^1_1$, (of $LCD_1$) is rotated for +α and $S^1_2$ (of $LCD_2$) is rotated for −α. This feature can be also confirmed by computer modeling showing that with left-handed LC-cells the angle α is preferably positive and with the right handed LC-cells the angle α is preferably negative)

Relative rotation between the intrinsic positive in-plane birefringence of the negative c-plate compensation films and the normal to the symmetry axes $S^1_1$ and $S^1_2$ of the residual positive in-plane birefringence of the STN LC layers for a small angle γ→the intrinsic positive in-plane birefringence of the compensation foil $R_1$ is rotated for +γ from the normal to the LC symmetry axis $S^1_1$ and the intrinsic positive in-plane birefringence of the compensation foil $R_1$ is rotated for −γ from the normal to the LC symmetry axis $S^1_2$. This feature can be also confirmed by computer modeling showing that with left-handed LC-cells the angle γ is preferably positive and with the right handed LC-cells the angle γ is preferably negative.

The above mentioned ±γ symmetry rotations still fulfill the requirement for ~perpendicular orientation of the intrinsic positive in-plane birefringence of the negative c-plate compensation films and the symmetry axes $S^1_1$ and $S^1_2$ of the residual positive in-plane birefringence of the STN LC layers in both LC cells ($LCD_1$ and $LCD_2$). Therefore the electric driving conditions remain as in the case of the Example 2 and the driving voltage for LCD light-switching filter is reduced by ≧10% (from 5.9 V to 5.2 V) compared to Example 1.

The additional symmetries, as described above, are hard to be understood without computer modeling. However the latter shows an important overall improvement of the angular dependence of the homogeneity of the light attenuation. The results of computer modeling are in excellent agreement with the experimental data. The proposed novel "super-symmetric" configuration of the LCD light filter meets the highest optical quality requirements related to the angular homogeneity of the protective shade according to International standard EN 379.

The results of the experimental evaluation of the LCD light switching filter manufactured according to the above Example 3 consist of the measurements of the angular dependence of the light incident at polar angle Θ=15° with respect to the normal to the filter plane (—limiting light incidence angle according to the EN 379 regulation) as well as full polar angle Θ and azimuth angle Φ measurements. The results are shown in the FIG. 10a, b.

It is obvious that the results for the dual HTLS LC-cell light switching filter are an order of magnitude better than with the present state-of-the-art products (TN LCD).

The measurements of the angular dependence of the protective shade of the protective LCD light-switching filters (FIG. 10) show that their optical performance is well within the requirements for the top optical performance (optical class 1/1/1/1) as required by the international regulation EN 379 and is in fact almost two times better than required by the said regulation.

It should be however emphasized, that the described Examples represent only three feasible working embodiments of the angularly compensated LCD welding filter according to the invention. Various modifications and variations can be made within the scope of this invention, especially in the choice of relative orientation of the polarizing films and the LC-molecular alignment as well as complementary LC-cell construction allowing adapting to the requirements of specific applications.

A typical example of possible modifications not described and/or shown in the Figures is a set of configurations resulting from the symmetry of the direction of light passing through the filter laminate as described in the FIG. 8. If the direction of light is reversed (input light $L_i$ to the LC-cell is changed to output light $L_o$ and vice versa in the patent text as well as in the FIGS. 1 and 8) then the input polarizer polarizes light along the symmetry axis ($S^1_1$ or $S^1_2$) through the acute angle of the LC alignment directions, the optimal position of the compensating layers R1, R2 within the LCD light-switching filter stack are swapped from below to the top of the LCD-cells (LCD1, LCD2), etc. . . . Such a configuration is yet another embodiment of the LCD light-switching filter according to the invention!

What is claimed is:

1. High contrast, wide viewing angle LCD light switching filter comprising two electrically controlled LC-cells (LCD1, LCD2) angularly compensated by two birefringent layers (R1, R2), adjacent to the either side of the said LC-cells (LCD1, respectively LCD2) and positioned between two mutually crossed pairs of polarizing films ($P_1$, $A_1$ and $P_2$, $A_2$), each of the said LC-cells (LCD1, LCD2) having a thin liquid crystal molecular layer ($d^a+d^b+e$) of highly twisted liquid crystal enclosed between two boundary glass plates (1$a^a$, 1$a^b$), the said plates (1$a^a$, 1$a^b$) being on an inner side covered by transparent electrodes (1$b^a$, 1$b^b$) and alignment layers (1$c^a$, 1$c^b$), characterized in that the alignment layers ($1c^a$, $1c^b$) on the transparent electrodes ($1b^a$, $1b^b$) covering the boundary glass plates ($1a^a$, $1a^b$) of both LC-cells (LCD1, LCD2) are oriented in such a way that in an optically open state of the LCD light switching filter, when no driving electric voltage (V=0) is applied to the transparent electrodes ($1b^a$, $1b^b$), the liquid crystal molecular layer ($d^a+d^b+e$) adopts a highly twisted molecular orientation with twist angles Φ between 120° to 240° and that the two birefringent layers (R1 respectively R2), adjacent to the said LC-cells (LCD1 respectively LCD2) are negative birefringent c-plates having a nominal negative birefringence with their optic axis oriented perpendicularly to the LCD light switching filter plane and exhibiting intrinsic positive in-plane birefringence aligned in-plane of the LCD light switching filter, said intrinsic positive birefringence being less than 10% of the nominal negative-birefringence, and that the two crossed pairs of polarizing films ($P_1$, $A_1$ and $P_2$, $A_2$) are oriented with respect to LC molecular alignment surface directions ($1r^a$, $1r^b$ respectively $2r^a$, $2r^b$) of each of the LC cells (LCD1, LCD2) in such a way that the light transmission axes of a first ($P_1$, $A_1$) of said pairs of polarizing films are aligned within a small angle α along symmetry axes ($S^1_1$, $S^2_1$) of the LC-molecular alignment surface directions ($1r^a$, $1r^b$) in a first LC-cell (LCD1) and that the light transmission axes of a second ($P_2$, $A_2$) of said pairs of polarizing films are aligned within a small angle α along symmetry axes ($S^1_2$, $S^2_2$) of the LC-molecular alignment surface directions ($2r^a$, $2r^b$) in a second LC-cell (LCD2), wherein said angle α is smaller than 15 degrees, allowing for the expansion of an overall viewing angle of the LCD light switching filter; wherein the LC-cells (LCD1, LCD2) provide a light transmission/driving voltage characteristics of high light transmission at driving voltages lower than a threshold voltage $V_{th}$ followed by a steep decay to low light transmission with increasing driving voltages as a first regime and a further less inclined decay of light transmission beginning at a limiting driving voltage $V_{LS}$ with further increasing driving voltages as a second, "low-slope" regime (LS) and that the LCD light switching filter is adapted to be operated in the second regime of the light transmission/driving voltage characteristics of the LC-cells (LCD1, LCD2) in an "optically-closed" state, wherein the light attenuation is varied only within the second regime being always greater than 10, and wherein the twist angle Φ of the said highly twisted liquid crystal in the LC-cells (LCD1, LCD2) is selected to adjust the slope of the light transmission/driving voltage characteristics of the LC-cells (LCD1, LCD2) in the "optically-closed" state and that the angle α of the relative alignment of the said two crossed pairs of polarizing films ($P_1$, $A_1$ and $P_2$, $A_2$) with respect to the LC molecular alignment surface directions ($1r^a$, $1r^b$ respectively $2r^a$, $2r^b$) is selected to optimize a required amplitude of electric driving signals to best fit with a driving electronics in particular with an available driving battery, wherein the twist angle Φ is varied between 210° and 240° and the relative alignment angle α between 2° and 15°.

2. High contrast, wide viewing angle LCD light switching filter according to claim 1 characterized in that a concentration of a chiral dopant in the said liquid crystal molecular layer ($d^a+d^b+e$) is selected to further optimize the slope of the light transmission vs. voltage characteristics in the said second regime (LS), wherein said concentration of the said chiral dopant is in the range between concentrations causing 5% and concentrations causing 120% of the twist angle Φ of the molecular orientation within the said liquid crystal molecular layer ($d^a+d^b+e$), when no driving voltage (V) is applied to it.

3. High contrast, wide viewing angle LCD light switching filter according to claim 1, characterized in that angle α between the said first pair of crossed polarizing films ($P_1$, $A_1$) and the said symmetry axes ($S^1_1$, $S^2_1$) in said first LC-cell (LCD1) and between the said second pair of crossed polarizing films ($P_2$, $A_2$) and the said symmetry axes ($S^1_2$, $S^2_2$) in the said second LC-cell (LCD2) is adjusted to maximize the overall viewing angle, while keeping the light attenuation within a cone of +/−15 degrees around the normal to the LCD light switching filter such that even at a maximum light attenuation of 100.000 the said light attenuation varies less than for a factor 1.6 around the average value within the said 15 degree cone angle and that the transmission axis of a light output polarizing film ($A_1$) of said first ($P_1$, $A_1$) of said pairs of polarizing films of the first LC-cell (LCD1) is aligned to be parallel within a small angle β to the transmission axis of a light input polarizing film ($P_2$) of said second ($P_2$, $A_2$) of said pairs of polarizing films of the second LC-cell (LCD2), wherein the said angle β is smaller or equal to 15 degrees.

4. High contrast, wide viewing angle LCD light switching filter according to claim 1, characterized in that the said two LC-cells (LCD1, LCD2) have a complementary configuration, in which all technical parameters are identical except for the liquid crystal molecular alignment directions ($2r^a$, $2r^b$) of the second LC-cell (LCD2), which are swapped for 90 degrees with respect to the first LC-cell (LCD1), so that the symmetry axis ($S^1_2$) through an acute angle between the molecular alignment directions ($2r^a$, $2r^b$) of the second LC-cell (LCD2) is perpendicular to the symmetry axis ($S^1_1$) through an acute angle between the molecular alignment directions ($1r^a$, $1r^b$) of the first LC-cell (LCD1).

5. High contrast, wide viewing angle LCD light switching filter according to claim 4, characterized in that a first (R1) of the negative-birefringent layers (R1, R2) is arranged between the either one of the said boundary glass plates ($1a^a$, $1a^b$) of the first LC-cell (LCD1) and the adjacent polarizing film ($P_1$) or ($A_1$) of said first ($P_1$, $A_1$) of said pairs of polarizing films and a second (R2) of the negative-birefringent layers (R1, R2) is arranged between the either one of the said boundary glass plates ($2a^a$, $2a^b$) of the second LC-cell (LCD2) and the adjacent polarizing film ($P_2$) or ($A_2$) of the second ($P_2$, $A_2$) of said pairs of polarizing films and that the negative-birefringent layers (R1, R2), an optical axis of which is perpendicular to a LCD light switching filter plane, exhibit the same negative optical retardation $\Delta n_R^- \times d_R^-$, where $\Delta n_R^-$ is the difference between the refractive indices of the ordinary and extraordinary light ray in the said negative-birefringent layers (R1, R2) and $d_R^-$ is the thickness of the said negative-birefringent layers (R1, R2), and that the negative-birefringent layers (R1 respectively R2) are further oriented relatively to the pairs of crossed polarizing films ($P_1$, $A_1$ respectively $P_2$, $A_2$) so that said intrinsic positive in-plane birefringence of the said layers is aligned with either one of the adjacent crossed polarizers ($P_1$, $A_1$ respectively $P_2$, $A_2$) and that an absolute value of a negative optical retardation $\Delta n_R^- \times d_R^-$ of the said negative-birefringent layers (R1, R2) is selected to be equal to the difference between an absolute value of a positive optical retardation $\Delta n_e^+ \times d_e^+$ of a homeotropically aligned part of the liquid crystal molecular layer (e) in said LC-cells (LCD1, LCD2) and an absolute value of a negative optical retardation $\Delta n_p^- \times d_p^-$ of the said pairs of polarizing films ($P_1$, $A_1$, $P_2$, $A_2$), where $\Delta n_e^+$ is the difference between the refractive indices of the ordinary and extraordinary light ray in the said homeotropically aligned part of the liquid crystal molecular layer (e), ($d_e^+$) is the thickness of a said homeotropically aligned liquid crystal molecular layer (e) and $\Delta n_p^-$ is the difference between the refractive indices of the ordinary and extraordinary light ray in the polarizing films ($P_1$, $A_1$, $P_2$, $A_2$) while $d_p^-$ is the thickness of the said polarizing films ($P_1$, $A_1$, $P_2$, $A_2$).

6. High contrast, wide viewing angle LCD light switching filter according to claim 4, characterized in that said birefringent layers (R1, R2) are negative c-plate birefringent films (R1, R2) with optical retardation values being in the range from 200 to 500 nm and are additionally oriented with respect to the said LC molecular alignment surface directions ($1r^a$, $1r^b$ respectively $2r^a$, $2r^b$) in such a way that the intrinsic positive in-plane birefringence of the negative c-plate birefringent films (R1 respectively R2) are substantially orthogonal to the residual positive in-plane birefringence of the LC layers in the LC-cells (LCD1 respectively LCD2) in their optically closed state and which are parallel to the LC molecular alignment symmetry axes ($S^1_1$, $S^2_1$), wherein an angle γ between the intrinsic positive in-plane birefringence of the negative c-plate birefringent films and the residual positive in-plane birefringence of the LC layers in the LC-cells is smaller than 15°.

7. High contrast, wide viewing angle LCD light switching filter according to claim 6 characterized in that a light input polarizing film ($P_1$) of a first ($P_1$, $A_1$) of said pairs of polarizing films for the first LC-cell (LCD1) is perpendicular within a small angle α to the symmetry axis ($S^1_1$) through an acute angle between the LC molecular alignment directions ($1r^a$, $1r^b$) of the first LC-cell (LCD1) and a light input polarizing film ($P_2$) of a second ($P_2$, $A_2$) of said pairs of polarizing films for the second LC-cell (LCD2) is perpendicular within a small angle α to the symmetry axis ($S^1_2$) through an acute angle between the liquid crystal molecular alignment directions ($2r^a$, $2r^b$) of the second LC-cell (LCD2), the said angle α being smaller than 15 degrees and that a first (R1) of the negative-birefringent layers (R1, R2) is arranged between the light output boundary glass plate ($1a^b$) of the first LC-cell (LCD1) and the adjacent light output polarizing film ($A_1$) and a second (R2) of the negative-birefringent layers (R1, R2) is arranged between the light output boundary glass plate ($2a^b$) of the second LC-cell (LCD2) and the adjacent light output polarizing film ($A_2$) and that both said negative-birefringent layers (R1, R2), the optic axes of which are perpendicular to a LCD light switching filter plane, exhibit the same negative optical retardation $\Delta n_R^- \times d_R^-$, where $\Delta n_R^-$ is the difference between the refractive indices of the ordinary and extraordinary light ray in the said negative-birefringent layers (R1, R2) and $d_R^-$ is the thickness of the said negative-birefringent layers (R1, R2), and that an absolute value of the negative optical retardation $\Delta n_R^- \times d_R^-$ of said negative-birefringent layers (R1, R2) is selected to be smaller than the difference between an absolute value of a positive optical retardation $\Delta n_e^+ \times d_e^+$ of a homeotropically aligned part of the liquid crystal molecular layer (e) in the LC-cells (LCD1, LCD2) and an absolute value of a negative optical retardation $\Delta n_p^- \times d_p^-$ of the said pairs of polarizing films ($P_1$, $A_1$, $P_2$, $A_2$) so that a resulting positive optical retardation $(\Delta n_e^+ \times d_e^+) - (\Delta n_p^- \times d_p^-) - (\Delta n_R^- \times d_R^-)$ in the direction of the normal to the LCD light switching filter, in combination with an in-plane residual positive optical retardation of boundary parts of the liquid crystal molecular layer ($d^a$, $d^b$) in both LC-cells (LCD1, LCD2) allows for rather efficient additional compensation of an angular dependence of the pairs of crossed polarizing films ($P_1$, $A_1$ and $P_2$, $A_2$), where $\Delta n_e^+$ is the difference between the refractive indices of the ordinary and extraordinary light ray in the homeotropically aligned part of the liquid crystal molecular layer (e), $d_e^+$ is the thickness of said homeotropically aligned part of the liquid crystal molecular layer (e) and $\Delta n_p^-$ is the difference between the refractive indices of the ordinary and extraordinary light ray in the polarizing films ($P_1$, $A_1$, $P_2$, $A_2$) while $d_p^-$ is the thickness of the said polarizing films ($P_1$, $A_1$, $P_2$, $A_2$).

8. High contrast, wide viewing angle LCD light switching filter according to claim 7, characterized in that the thickness $d_R^-$ of the said negative-birefringent layers (R1, R2) is selected to be such that the absolute value of their negative optical retardation $\Delta n_R^- \times d_R^-$ is at least 100 nm but not more than 250 nm smaller than the difference between the absolute value of the positive optical retardation $\Delta n_e^+ \times d_e^+$ of the homeotropically aligned part of the liquid crystal molecular layer (e) in the LC-cells (LCD1, LCD2) and an absolute value of the negative optical retardation $\Delta n_p^- \times d_p^-$ of the said pairs of polarizing films ($P_1$, $A_1$, $P_2$, $A_2$).

9. High contrast, wide viewing angle LCD light switching filter according to claim 1, characterized in that the said two LC-cells (LCD1, LCD2) exhibit also a further complementary configuration, in which all technical parameters are identical for both complementary parts except for liquid crystal (LC) molecular alignment directions ($2r^a$, $2r^b$) of the second LC-cell (LCD2), which are swapped with respect to the first LC-cell (LCD1) in such a way that the symmetry axis ($S^1_2$) through an acute angle between the molecular alignment directions ($2r^a$, $2r^b$) of the second LC-cell (LCD2) is perpendicular to the symmetry axis ($S^1_1$) through an acute angle between the molecular alignment directions ($1r^a$, $1r^b$) of the first LC-cell (LCD1) and liquid crystal (LC) chiral doping, which is changed in such a way that the LC molecular twist (Φ) in the first LC-cell (LCD1) adopts a reverse chirality as the LC molecular twist (Φ) in the second LC-cell (LCD2), e.g. LC-cell (LCD1) exhibiting a left handed twist of the LC molecular orientation and LC-cell (LCD2) exhibiting a right handed twist in the electrically non-driven state or vice versa.

10. High contrast, wide viewing angle LCD light switching filter according to claim 9, characterized in that the two LCD light shutters constituting the LCD light switching filter, comprising first crossed polarizing filters ($P_1$, $A_1$), first LC-cell (LCD1), first negative-birefringent layer (R1) respectively second crossed polarizing filters ($P_2$, $A_2$), second LC-cell (LCD2), second negative-birefringent layer (R2) are constructed to adopt a "mirror image" of one another such that:

LC alignment in the first LC-cell (LCD1) exhibits the same alignment twist angle (Φ) but opposite chirality as the LC alignment in the second LC-cell (LCD2) and LC alignment symmetry axis ($S^1_1$) in the first LC-cell (LCD1) is substantially perpendicular within a small angle $\beta \leq 15°$ to the LC alignment symmetry axis ($S^1_2$) in the second LC-cell (LCD2) and relative angle ($\alpha_1$) between the LC alignment symmetry axes of the first LC-cell (LCD1) with the adjacent crossed polarizers (P1, A1) has the opposite sign (+/−) with respect to the relative angle ($\alpha_2$) between the LC alignment symmetry axes of the second LC-cell (LCD2) with the adjacent crossed polarizers (P2, A2) and relative alignment within a small angle $\gamma_1 \leq 12°$ of the intrinsic positive in-plane birefringence of the negative-birefringent layer (R1) with the LC alignment symmetry axis ($S^2_1$) of the first LC-cell (LCD1) has the opposite sign (+/−) with respect to the relative alignment within a small angle $\gamma_2 \leq 12°$ of the intrinsic positive in-plane birefringence of the negative-birefringent layer (R2) with the LC alignment symmetry axis ($S^2_2$) of the second LC-cell (LCD2).

11. High contrast, wide viewing angle LCD light switching filter according to claim 10 characterized in that a light input polarizing film ($P_1$) of a first ($P_1$, $A_1$) of said pairs of polarizing films for the first LC-cell (LCD1) is perpendicular within a small angle (+$\alpha$) to the symmetry axis ($S^1_1$) through an acute angle between the LC molecular alignment directions ($1r^a$, $1r^b$) of the first LC-cell (LCD1) and a light input polarizing film ($P_2$) of a second ($P_2$, $A_2$) of the said pairs of polarizing films for the second LC-cell (LCD2) is perpendicular within a small angle (−$\alpha$) to the symmetry axis ($S^1_2$) through an acute angle between the liquid crystal molecular alignment directions ($2r^a$, $2r^b$) of the second LC-cell (LCD2), the said angle ($\alpha$) being smaller than 15 degrees and that a first (R1) of said negative-birefringent layers (R1, R2) is arranged between the light output boundary glass plate ($1a^b$) of the first LC-cell (LCD1) and the adjacent light output polarizing film ($A_1$) and a second (R2) of said negative-birefringent layers (R1, R2) is arranged between the light output boundary glass plate ($2a^b$) of the second LC-cell (LCD2) and the adjacent light output polarizing film ($A_2$) and that both said negative-birefringent layers (R1, R2), the optic axes of which are perpendicular to a LCD light switching filter plane, exhibit the same negative optical retardation $\Delta n_R^- \times d_R^-$, where $\Delta n_R^-$ is the difference between the refractive indices of the ordinary and extraordinary light ray in the said negative-birefringent layers (R1, R2) and $d_R^-$ is the thickness of the said negative-birefringent layers (R1, R2), and that an absolute value of the negative optical retardation $\Delta n_R^- \times d_R^-$ of said negative-birefringent layers (R1, R2) is selected to be smaller than the difference between an absolute value of a positive optical retardation $\Delta n_e^+ \times d_e^+$ of a homeotropically aligned part of the liquid crystal molecular layer (e) in the LC-cells (LCD1, LCD2) and an absolute value of a negative optical retardation $\Delta n_p^- \times d_p^-$ of the said pairs of polarizing films ($P_1$, $A_1$, $P_2$, $A_2$) so that a resulting positive optical retardation ($\Delta n_e^+ \times d_e^+$)−($\Delta n_p^- \times d_p^-$)−($\Delta n_R^- \times d_R^-$) in the direction of the normal to the LCD light switching filter, in combination with an in-plane residual positive optical retardation of boundary parts of the liquid crystal molecular layer ($d^a$, $d^b$) in both LC-cells (LCD1, LCD2) allows for rather efficient additional compensation of an angular dependence of the pairs of crossed polarizing films ($P_1$, $A_1$ and $P_2$, $A_2$), where $\Delta n_e^+$ is the difference between the refractive indices of the ordinary and extraordinary light ray in the homeotropically aligned part of the liquid crystal molecular layer (e), $d_e^+$ is the thickness of said homeotropically aligned part of the liquid crystal molecular layer (e) and $\Delta n_p^-$ is the difference between the refractive indices of the ordinary and extraordinary light ray in the polarizing films ($P_1$, $A_1$, $P_2$, $A_2$) while $d_p^-$ is the thickness of the said polarizing films ($P_1$, $A_1$, $P_2$, $A_2$).

12. High contrast, wide viewing angle LCD light switching filter according to claim 11, characterized in that the thickness $d_R^-$ of the said negative-birefringent layers (R1, R2) is selected to be such that the absolute value of their negative optical retardation $\Delta n_R^- \times d_R^-$ is at least 100 nm but not more than 250 nm smaller than the difference between the absolute value of the positive optical retardation $\Delta n_e^+ \times d_e^+$ of the homeotropically aligned part of the liquid crystal molecular layer (e) in the LC-cells (LCD1, LCD2) and an absolute value of the negative optical retardation $\Delta n_p^- \times d_p^-$ of the said pairs of polarizing films ($P_1$, $A_1$, $P_2$, $A_2$).

13. High contrast, wide viewing angle LCD light switching filter according to claim 1, characterized in that angle $\alpha$ between the said first pair of crossed polarizing films ($P_1$, $A_1$) and the said symmetry axes ($S^1_1$, $S^2_1$) in said first LC-cell (LCD1) and between the said second pair of crossed polarizing films ($P_2$, $A_2$) and the said symmetry axes ($S^1_2$, $S^2_2$) in the said second LC-cell (LCD2) is adjusted to maximize the overall viewing angle, while keeping the light attenuation within a cone of +/−15 degrees around the normal to the LCD light switching filter such that even at a maximum light attenuation of 130.000 the said light attenuation varies within the said 15 degree cone angle less than for a factor 1.6 around the value of the light attenuation at the normal light incidence and that the transmission axis of a light output polarizing film ($A_1$) of said first ($P_1$, $A_1$) of said pairs of polarizing films of the first LC-cell (LCD1) is aligned to be parallel within a small angle $\beta$ to the transmission axis of a light input polarizing film ($P_2$) of said second ($P_2$, $A_2$) of said pairs of polarizing films of the second LC-cell (LCD2), wherein the said angle $\beta$ is smaller or equal to 15 degrees.

* * * * *